United States Patent
Hsiao et al.

(10) Patent No.: US 9,150,828 B2
(45) Date of Patent: Oct. 6, 2015

(54) LACTOBACILLUS MUTANT, NUCLEOTIDE SEQUENCE FOR LACTOBACILLUS MUTANT AND PRIMERS FOR NUCLEOTIDE SEQUENCE OF LACTOBACILLUS MUTANT

(71) Applicants: Hsia-Ching Hsiao, Taipei (TW); Tzu-Ming Pan, Sijhih (TW)

(72) Inventors: Hsia-Ching Hsiao, Taipei (TW); Tzu-Ming Pan, Sijhih (TW)

( * ) Notice: Subject to any disclaimer, the term of this patent is extended or adjusted under 35 U.S.C. 154(b) by 0 days.

(21) Appl. No.: 14/142,810

(22) Filed: Dec. 28, 2013

(65) Prior Publication Data

US 2014/0242672 A1    Aug. 28, 2014

Related U.S. Application Data

(63) Continuation-in-part of application No. 12/946,817, filed on Nov. 15, 2010, now abandoned.

(51) Int. Cl.
  *C12N 1/20*    (2006.01)
  *C12P 7/56*    (2006.01)
  *C12R 1/225*   (2006.01)

(52) U.S. Cl.
  CPC ... *C12N 1/20* (2013.01); *C12P 7/56* (2013.01); *C12R 1/225* (2013.01)

(58) Field of Classification Search
  None
  See application file for complete search history.

(56) References Cited

PUBLICATIONS

Tsai et al. International Journal of Food Microbiology. 2008;128:219-225.*
BD. Lactobacilli MRS agar, Lactobacilli MRS broth. 2009;1-2.*
Lin et al. J Ind Microbiol Biotechnol (2004) 31:559 564.*

* cited by examiner

*Primary Examiner* — Christian Fronda
(74) *Attorney, Agent, or Firm* — Anova Law Group, PLLC

(57) ABSTRACT

The present invention relates to a *lactobacillus* mutant, a nucleotide sequence for *lactobacillus* mutant, and primers for nucleotide sequence of *lactobacillus* mutant. The *lactobacillus* mutant is *Lactobacillus paracasei* subsp. *paracasei* NTU 101 having the nucleotide sequence of SEQ ID NO 1, and deposited with Deutsche Sammlung von Mikroorganismen and Zellkulturen GmbH (DSMZ, Inhoffenstr. 7B, D-38124 Braunschweig, Germany) on Nov. 18, 2013, wherein the accession number of *Lactobacillus paracasei* subsp. *paracasei* NTU 101 is DSM 28047. In the present invention, a nucleotide sequence for NTU 101 and the primers for the nucleotide sequence are proposed in order to facilitate the person skilled in *Lactobacillus* filed capable of carrying out the strain (mutant) identification of the NTU 101 according to the present invention. Moreover, the person skilled in *Lactobacillus* filed can also rapidly complete the strain (mutant) identification of the NTU 101 by using DNA molecular marker technology, without culturing any isolated *Lactobacillus* strain or live *Lactobacillus* bacteria.

5 Claims, 11 Drawing Sheets

LACTOBACILLUS MUTANT, NUCLEOTIDE SEQUENCE FOR LACTOBACILLUS MUTANT AND PRIMERS FOR NUCLEOTIDE SEQUENCE OF LACTOBACILLUS MUTANT

CROSS-REFERENCE TO RELATED APPLICATION

This application is a continuation-in-part of U.S. application Ser. No. 12/946,817, filed on Nov. 15, 2010, the content of which is incorporated herein by reference in its entirety.

SEQUENCE LISTING

The instant application contains a Sequence Listing which has been submitted in ASCII format via EFS-Web and is hereby incorporated by reference in its entirety. The ASCII copy is named sequence.txt and is 2,105 bytes in size.

BACKGROUND OF THE INVENTION

1. Field of the Invention

The present invention relates to a *lactobacillus* mutant, and more particularly to a *Lactobacillus paracasei* subsp. *paracasei* NTU 101, a nucleotide sequence for *Lactobacillus* NTU 101 and primers for nucleotide sequence of *Lactobacillus* NTU 101.

2. Description of the Prior Art

Lactate bacteria are one kind of bacteria able to metabolize carbohydrate and then produce over 50% lactic acid; for example, *Lactobacillus, Streptococcus* and *Leuconostoc*. Because the fermented milk products are traditional and historical drinks for human, the lactate bacteria are regarded as a safe bacteria and a representative intestinal probiotics. Moreover, the lactate bacteria are one of the important probiotics, which is able to enhance the quality of intestinal flora through the following ways:
(1) producing organic acids and reducing intestinal pH value;
(2) absorbing nutrients by way of competing with pernicious bacteria;
(3) adhering to intestinal epithelium for reducing the growth sites of pernicious bacteria; and
(4) producing antibiotic substances.

Nowadays, a variety of fermented milk products have been proven their ability of increasing the intestinal probiotics after the related human experimentation is completed. *Lactobacillus paracasei* subsp. *paracasei* NTU 101 is an excellent local *Lactobacillus* strain, and which is studied and developed by Tzu-Ming PAN, the graduate chair of Institute of Microbiology and Biochemistry of National Taiwan University, and the R&D team thereof. Besides, currently, the health-care characteristics of improving the quality of intestinal flora, decreasing the blood pressure, the hyperlipidemia and the cholesterol, and anti-allergy of the *Lactobacillus paracasei* subsp. *paracasei* NTU 101 as well as the its related fermented products have been proven, and the *L. paracasei* subsp. *paracasei* NTU 101 is successful to be commercialized. However, in spite of that, the strain (mutant) identification and the DNA molecular marker of the *L. paracasei* subsp. *paracasei* NTU 101 does still not be carried out, wherein the DNA molecular marker technology is usually used for identifying the DNA sequence or the RAPD genetic variation map.

Accordingly, in view of the specific DNA sequence, the specific RAPD genetic variation map, and the DNA molecular marker of the *L. paracasei* subsp. *paracasei* NTU 101 still does not be finished, the inventor of the present application has made great efforts to make inventive research thereon and eventually provided a *Lactobacillus* mutant, a nucleotide sequence for *Lactobacillus* mutant and primers for nucleotide sequence of *Lactobacillus* mutant.

SUMMARY OF THE INVENTION

The primary objective of the present invention is to provide a *Lactobacillus paracasei* subsp. *paracasei* NTU 101, a nucleotide sequence for *Lactobacillus* NTU 101 and primers for nucleotide sequence of *Lactobacillus* NTU 101, therefore the person skilled in *Lactobacillus* filed is able to carried out the strain (mutant) identification of the *Lactobacillus paracasei* subsp. *paracasei* NTU 101 according to the present invention. Moreover, the person skilled in *Lactobacillus* filed can also rapidly complete the strain (mutant) identification of the *Lactobacillus* NTU 101 by using DNA molecular marker technology, without culturing any isolated *Lactobacillus* strain or live *Lactobacillus* bacteria.

Accordingly, to achieve the primary objective of the present invention, the inventor of the present invention provides a *Lactobacillus* mutant, which is *Lactobacillus paracasei* subsp. *paracasei* NTU 101 having a nucleotide sequence of SEQ ID NO 1, and deposited with Deutsche Sammlung von Mikroorganismen and Zellkulturen GmbH (DSMZ, Inhoffenstr. 7B, D-38124 Braunschweig, Germany) on Nov. 18, 2013, wherein the accession number of the *Lactobacillus paracasei* subsp. *paracasei* NTU 101 is DSM 28047. Moreover, the nucleotide sequence of the *Lactobacillus paracasei* subsp. *paracasei* NTU 101 can be formed by treating the RAPD (Random Amplification of Polymorphic DNA) and the PCR (Polymerase Chain Reaction) process to a plurality of specific primers, wherein the specific primers comprising a first nucleotide sequence of SEQ ID NO 2 and a second nucleotide sequence of SEQ ID NO 3.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
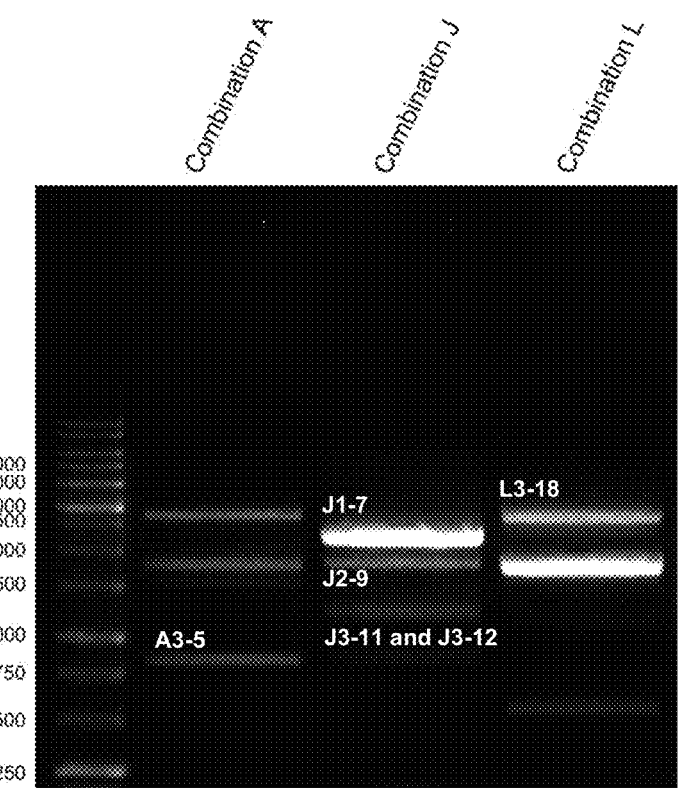
FIG. 1 is an image diagram of a RAPD genetic variation map of the primer compounds of A, J and L.

To more clearly describe a *Lactobacillus* Mutant, Nucleotide Sequences for the *Lactobacillus* Mutant and Primers for the Nucleotide Sequence of the *Lactobacillus* Mutant according to the present invention, embodiments of the present invention will be described in detail with reference to the attached drawings hereinafter.

NTU 101 *Lactobacillus* mutant is an excellent local *lactobacillus* strain, and which is studied and developed by Tzu- Ming PAN, the graduate chair of Institute of Microbiology and Biochemistry of National Taiwan University, and the R&D team thereof. In the present invention, the *Lactobacillus paracasei* subsp. *paracasei* NTU 101 having a specific nucleotide sequence of SEQ ID NO 1 was deposited with Deutsche Sammlung von Mikroorganismen and Zellkulturen GmbH (DSMZ, Inhoffenstr. 7B, D-38124 Braunschweig, Germany) on Nov. 13, 2009, and was given accession number DSM 28047

The *Lactobacillus paracasei* subsp. *paracasei* NTU 101 includes the characteristics of: gram-positive, lacking catalase, having the ability of curding, acid resistance ability, alkaline resistance ability, bile salt resistance ability, facultative heterogeneous fermentation, producing L(+)-lactate, having excellent ability of immune regulation. The basic culture medium for *Lactobacillus paracasei* subsp. *paracasei* NTU 101 is MRS medium, wherein the best culture temperature is 30° C., the best culture time is 24 hours, the best culture pH value is 6.5, the best culture pressure is 1atm; moreover, the *Lactobacillus paracasei* subsp. *paracasei* NTU 101 needs microaerophilic growth.

Moreover, please refer to following table 1, which records and lists the amount of lactic acid produced by the *Lactobacillus paracasei* subsp. *paracasei* NTU 101 cultured in an identical culture medium containing different carbon sources, wherein the carbon sources are Glucose, Galactose, D-ribose, Xylose, Fructose, α-Lactose, Maltose, Sucrose, Trehalose, Raffinose, myo-Inositol, Sorbitol, D-mannitol, Citric acid, Dextrin, Starch, and Molasses, respectively.

TABLE 1

| Carbon source | viable count (Log CFU/mL) | pH value | Production amount of lactic acid (g/L) |
|---|---|---|---|
| Glucose | 9.43 | 3.73 | 17.48 |
| Galactose | 9.33 | 3.70 | 11.33 |
| D-ribose | 9.54 | 4.07 | 7.25 |
| Xylose | 8.94 | 6.37 | 0.40 |
| Fructose | 8.20 | 3.75 | 14.00 |
| α-Lactose | 9.26 | 3.87 | 11.64 |
| Maltose | 9.45 | 4.16 | 8.55 |
| Sucrose | 9.01 | 3.78 | 13.90 |
| Trehalose | 9.04 | 3.79 | 13.26 |
| Raffinose | 8.78 | 5.23 | 1.80 |
| myo-Inositol | 8.89 | 6.48 | 0.41 |
| Sorbitol | 9.65 | 4.15 | 7.49 |
| D-mannitol | 9.44 | 3.81 | 16.21 |
| Citric acid | 7.05 | 6.41 | 0.28 |
| Dextrin | 9.38 | 5.35 | 0.86 |
| Starch | 9.24 | 5.82 | 0.30 |
| Molasses | 9.70 | 4.50 | 6.02 |

Besides, please refer to following table 2, which records and lists the amount of lactic acid produced by the *Lactobacillus paracasei* subsp. *paracasei* NTU 101 cultured in an identical culture medium containing different nitrogen sources, wherein the nitrogen sources are Yeast extract, Beef extract, Peptone, Soytone, Tryptose, Corn-steep liquor, Casein, Urea, Ammonium citrate, and Ammonium sulfate, respectively. Therefore, through the listed data of the tables 1 and 2, the lactate-producing ability of the *Lactobacillus paracasei* subsp. *paracasei* NTU 101 of the present invention has been proven.

TABLE 2

| Nitrogen source | viable count (Log CFU/mL) | pH value | Production amount of lactic acid (g/L) |
|---|---|---|---|
| Yeast extract | 8.14 | 3.54 | 8.29 |
| Beef extract | 8.89 | 4.22 | 2.74 |
| Peptone | 8.95 | 3.74 | 5.91 |
| Soytone | 8.30 | 3.90 | 5.82 |
| Tryptose | 8.84 | 3.87 | 4.45 |
| Corn-steep liquor | 9.14 | 4.14 | 4.11 |
| Casein | 8.27 | 4.68 | 1.77 |
| Urea | 6.89 | 5.96 | 0.02 |
| Ammonium citrate | 7.09 | 6.04 | 0.08 |
| Ammonium sulfate | 6.69 | 5.84 | 0.07 |

Next, in order to identify the nucleotide sequence of the *Lactobacillus paracasei* subsp. *paracasei* NTU 101, 20 random primers are purchased from MDBio, Inc., located in Taipei of ROC, and the related information of the 20 random primers are listed in following table 3. Therefore, the 20 random primers are re-dissolved to 100 μM by using sterile water, and stored in a 20° C. environment.

TABLE 3

| Primer ID | Primer Sequence (5'→3') |
|---|---|
| B01 | GTTTCGCTCC |
| B02 | TGATCCCTGG |
| B03 | CATCCCCCTG |
| B04 | GGACTGGAGT |
| B05 | TGCGCCCTTC |
| B06 | TGCTCTGCCC |
| B07 | GGTGACGCAG |
| B08 | GTCCACACGG |
| B09 | TGGGGGACTC |
| B10 | CTGCTGGGAC |
| D11 | AGCGCCATTG |
| D12 | CACCGTATCC |
| D13 | GGGGTGACGA |
| D14 | CTTCCCCAAG |
| D15 | CATCCGTGCT |
| D16 | AGGGCGTAAG |
| D17 | TTTCCCACGG |
| D18 | GAGAGCCAAC |
| D19 | CTGGGGACTT |
| D20 | ACCCGGTCAC |

Continuously, please refer to following table 4, which recorded and listed 16 primer compounds, wherein the 16 primer compounds are prepared by mixing the 20 random primers and each of the 16 primer compounds have a final concentration of 1 μM. Furthermore, the 16 primer compounds would be amplified to form a probable nucleotide sequence of the *Lactobacillus paracasei* subsp. *paracasei* NTU 101 by way of being treated the RAPD (Random Amplification of Polymorphic DNA) and the PCR (Polymerase Chain Reaction) process.

TABLE 4

| primer compound | primers |
|---|---|
| A | B01, B02, D11, and D12 |
| B | B03, B04, D13, and D14 |
| C | B05, B06, D15, and D16 |
| D | B07, B08, D17, and D18 |
| E | B09, B10, D19, and D20 |
| F | B07, B08, B09, and D10 |
| G | D11, D12, D13, and D14 |
| H | D15, D16, D17, and D18 |
| I | B01, B02, D13, and D14 |
| J | B03, B04, D15, and D16 |
| K | B05, B06, D17, and D18 |
| L | B08, B09, D19, and D20 |
| M | B05, B06, D11, and D20 |
| N | B03, B04, D11, and D20 |
| O | B07, B08, D11, and D20 |
| P | B09, B10, D11, and D20 |

After the 16 primer compounds are prepared, the 16 primer compounds are next treated with a polymerase chain reaction (PCR) process. The polymerase chain reaction cocktail contains 3 ng DNA, 80 nM primers, a 1× Exsel reaction buffer, 5 U Exsel DNA polymerase (Bertec Enterprise, Taipei, Taiwan), and 200 M dNTPs. The reaction conditions of the PCR is as described: 95° C. (5 min) for heating; 95° C. (30 sec) for heating; 25° C. (3 min) for adhesion and 70° C. (3 min) for extension (35 cycles); and 70° C. (7 min) for extension.

Moreover, after completing the PCR process, it is able to execute the electrophoresis analysis for the PCR products by using 1% agarose gel. Next, the agarose gels of the PCR products are dyed for 30 min by using the dying agent of SYBR Safe (Life Technologies Corporation). Eventually, after 20 min destain, the dyed agarose gels of the PCR products are disposed into a blue light (488 nm) box for observing and taking image picture by using an image process system. Furthermore, the dyed agarose gels are divided to a plurality of segments by using FavorPrep™ Gel/PCR Purification Kit (Favorgen biotech Corp), and then the cloning of the agarose gel segments are finished by using T&ATM Cloning Kit (Yeastern Biotech Co., Ltd., Taipei, Taiwan). Finally, the specific nucleotide sequence of the *Lactobacillus paracasei* subsp. *paracasei* NTU 101 is identified.

Please refer to FIG. 1, there is shown an image diagram of a RAPD genetic variation map of the primer compounds of A, J and L. In the 16 primer compounds listed in above table 4, as shown in FIG. 1, there are only the primer compounds of J and especially A and L can be amplified and form the RAPD genetic variation map revealing the specificity of *Lactobacillus paracasei* subsp. *paracasei* NTU 101. Next, in order to further confirm the specificity of *Lactobacillus paracasei* subsp. *paracasei* NTU 101, as shown in following table 5, there is a *Lactobacillus casei* group having the genetic relationship to the *L. paracasei* subsp. *paracasei*, and the *Lactobacillus casei* group including 12 *L. paracasei*, 10 *L. casei*, 7 *L. rhamnosus*, and 3 *L. zeae*.

TABLE 5

| Microorganism | ID/BCRC |
|---|---|
| *Lactobacillus casei* | BCRC 10358 |

TABLE 5-continued

| Microorganism | ID/BCRC |
|---|---|
| *Lactobacillus casei* | BCRC 10697T |
| *Lactobacillus casei* | BCRC 11197 |
| *Lactobacillus casei* | BCRC 12272 |
| *Lactobacillus casei* | BCRC 14025 |
| *Lactobacillus casei* | BCRC 16093 |
| *Lactobacillus casei* | BCRC 16094 |
| *Lactobacillus casei* | BCRC 17001 |
| *Lactobacillus casei* | BCRC 17004 |
| *Lactobacillus casei* | BCRC 17487 |
| *Lactobacillus paracasei* subsp. *paracasei* | BCRC 12188 |
| *Lactobacillus paracasei* subsp. *paracasei* | BCRC 12248T |
| *Lactobacillus paracasei* subsp. *paracasei* | BCRC 14001 |
| *Lactobacillus paracasei* subsp. *paracasei* | BCRC 14023 |
| *Lactobacillus paracase* subsp. *paracasei* | BCRC 16100 |
| *Lactobacillus paracasei* subsp. *paracasei* | BCRC 17002 |
| *Lactobacillus paracasei* subsp. *paracasei* | BCRC 17483 |
| *Lactobacillus paracasei* subsp. *paracasei* | BCRC 17484 |
| *Lactobacillus paracasei* subsp. *tolerans* | BCRC 17485 |
| *Lactobacillus paracasei* subsp. *paracasei* | BCRC 17488 |
| *Lactobacillus paracasei* subsp. *paracasei* | BCRC 17489 |
| *Lactobacillus paracasei* | BCRC 80062 |
| *Lactobacillus zeae* | BCRC 17647T |
| *Lactobacillus zeae* | BCRC 17942T |
| *Lactobacillus zeae* | BCRC 80156 |
| *Lactobacillus rhamnosus* | BCRC 10940T |
| *Lactobacillus rhamnosus* | BCRC 11673 |
| *Lactobacillus rhamnosus* | BCRC 12249 |
| *Lactobacillus rhamnosus* | BCRC 14027 |
| *Lactobacillus rhamnosus* | BCRC 16095 |
| *Lactobacillus rhamnosus* | BCRC 17006 |
| *Lactobacillus rhamnosus* | BCRC 17007 |
| *Lactobacillus rhamnosus* | BCRC 80065 |

Figure 2A:
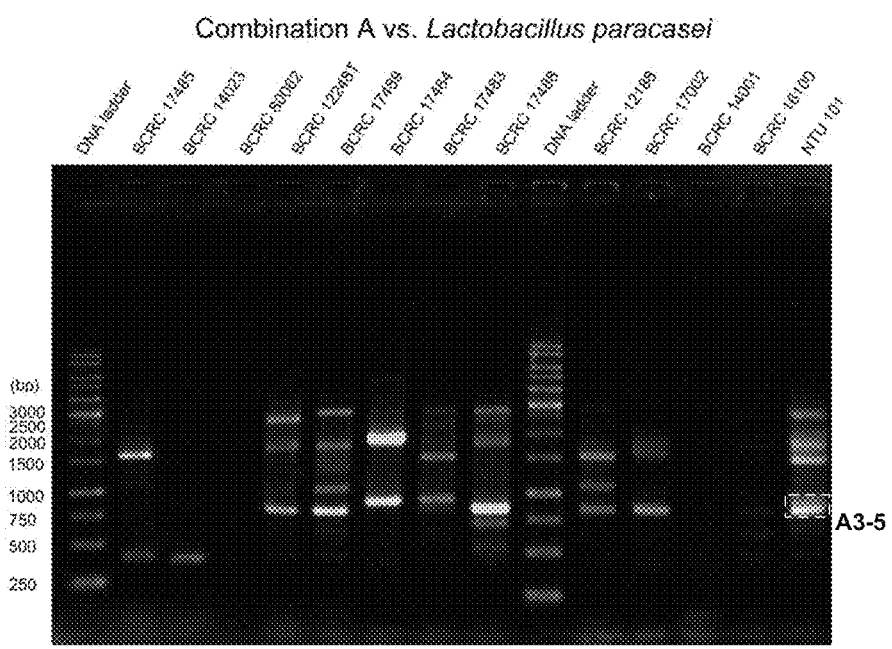
FIGS. 2A, 2B and 2C are shown comparing RAPD genetic variation maps of the primer compound A and *Lactobacillus casei* group.
Figure 2B:
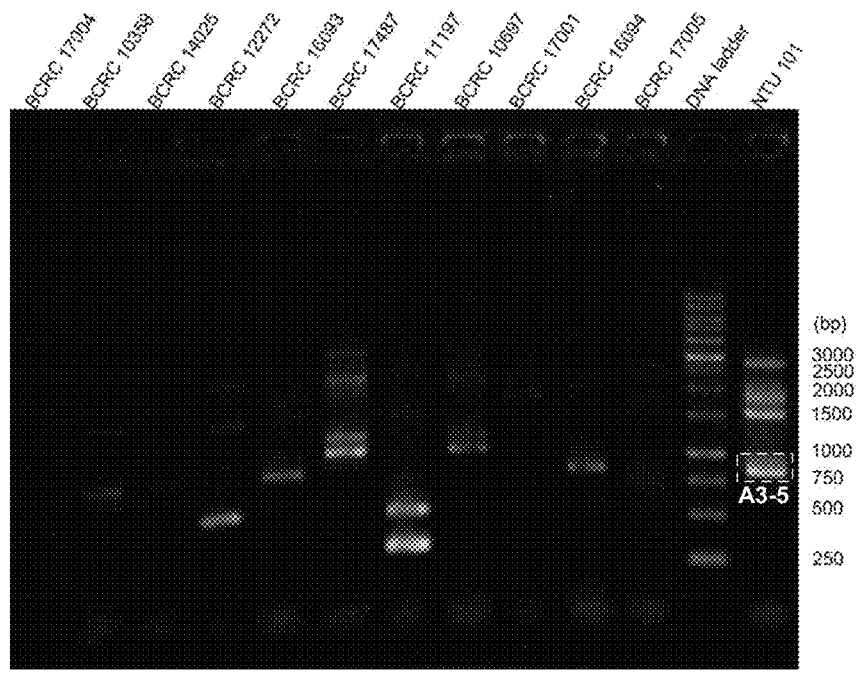
Figure 2C:
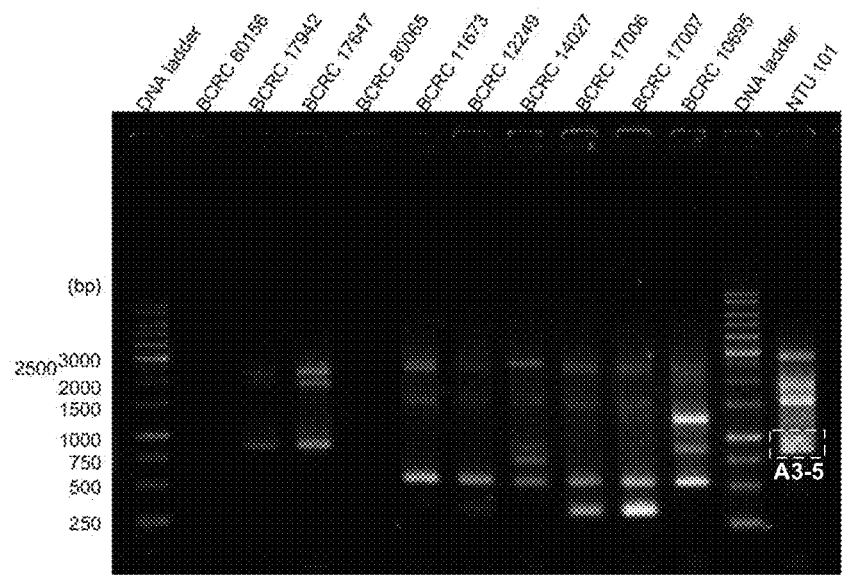

Please refer to FIGS. 2A, 2B and 2C, there are shown comparing RAPD genetic variation maps of the primer compound A and the *Lactobacillus casei* group. As shown in FIG. 2A, obviously, there has a large sequence difference between the (nucleotide) sequence of the RAPD genetic variation map of primer compound A and the sequence of the RAPD genetic variation map of the *Lactobacillus paracasei*. Besides, as shown in FIG. 2B, apparently, there has a large sequence difference between the (nucleotide) sequence of the RAPD genetic variation map of primer compound A and the sequence of the RAPD genetic variation map of the *Lactobacillus casei*. Moreover, as shown in FIG. 2C, distinctly, there has a large sequence difference between the (nucleotide) sequence of the RAPD genetic variation map of primer compound A and the sequence of the RAPD genetic variation map of the *Lactobacillus zeae* and the *Lactobacillus rhamnosus*. The distinctiveness of the RAPD genetic variation map of primer compound A is came from the primers B02 and D11, and this distinctive primer compound A is further marked as A3-5. Through the Sequence Listing, it is able to know that the nucleotide sequence of A3-5 is identified as SEQ ID NO 1 and includes the sequence length of 838 bp; besides, the nucleotide sequence of primer B02 is identified as SEQ ID NO 2 and includes the sequence length of 10 bp; moreover, the nucleotide sequence of primer D11 is identified as SEQ ID NO 3 and includes the sequence length of 10 bp.

Figure 3A:
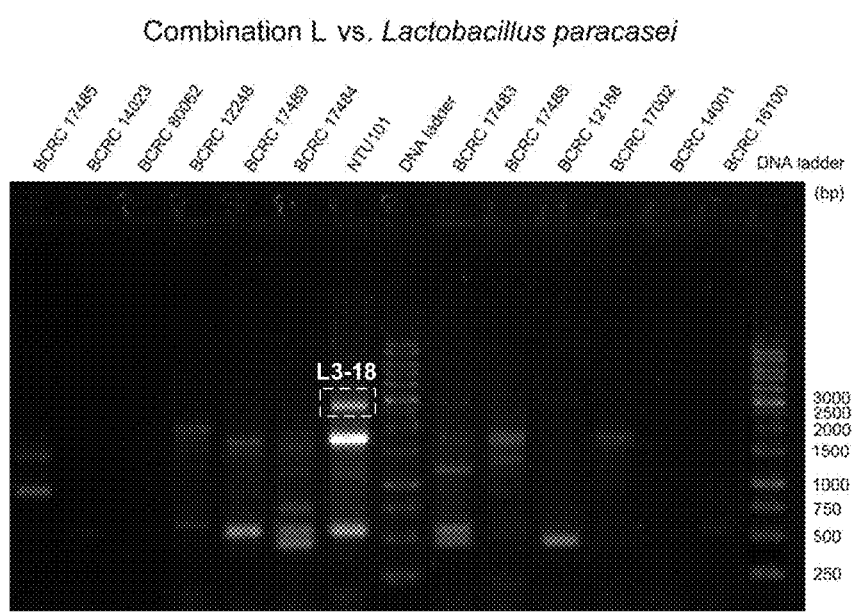
FIGS. 3A, 3B and 3C, are shown comparing RAPD genetic variation maps of the primer compound L and the *Lactobacillus casei* group.
Figure 3B:
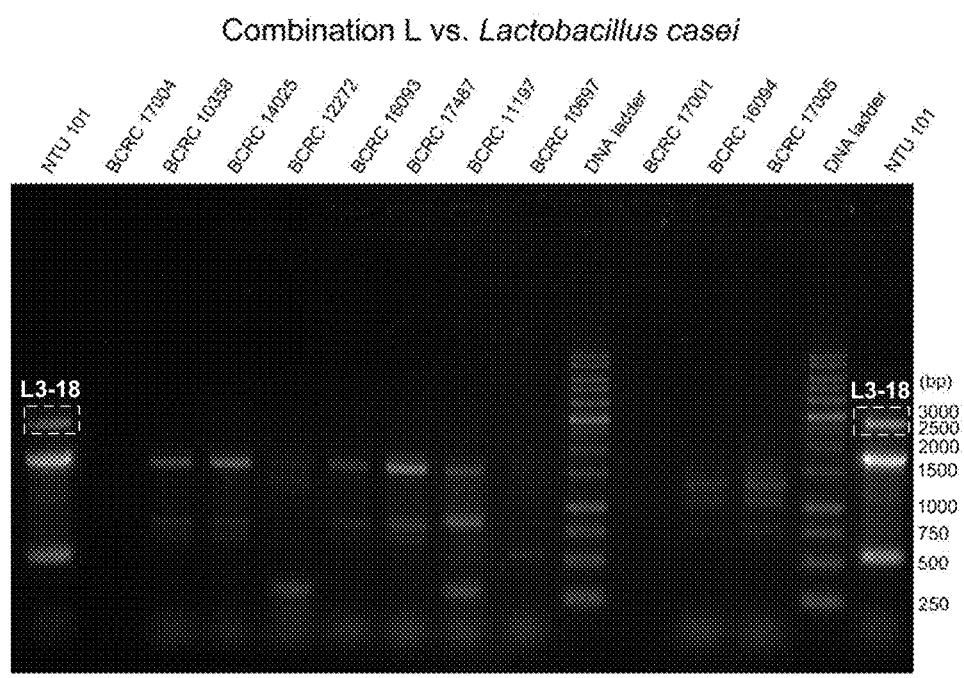
Figure 3C:
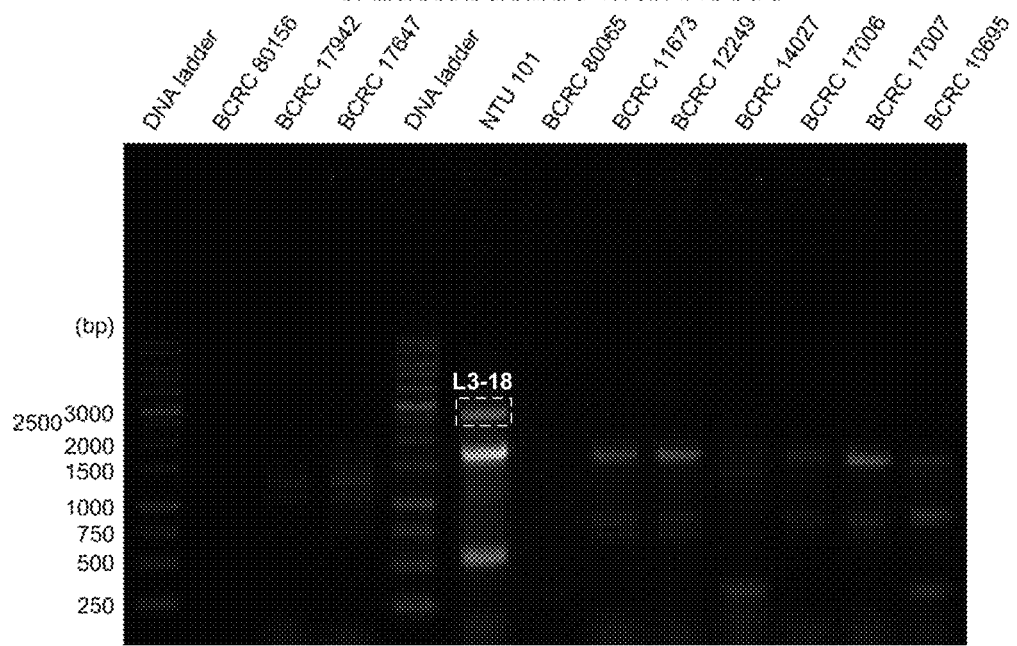

Continuously, please refer to FIGS. 3A, 3B and 3C, there are shown comparing RAPD genetic variation maps of the primer compound L and the *Lactobacillus casei* group. As shown in FIG. 3A, obviously, there has a large sequence difference between the (nucleotide) sequence of the RAPD genetic variation map of primer compound L and the sequence of the RAPD genetic variation map of the *Lactobacillus paracasei*. Besides, as shown in FIG. 3B, apparently, there has a large sequence difference between the (nucleotide) sequence of the RAPD genetic variation map of primer compound L and the sequence of the RAPD genetic variation map of the *Lactobacillus casei*. Moreover, as shown in FIG. 3C, distinctly, there has a large sequence difference between the (nucleotide) sequence of the RAPD genetic variation map of primer compound L and the sequence of the RAPD genetic variation map of the *Lactobacillus zeae* and the *Lactobacillus rhamnosus*. The distinctiveness of the RAPD genetic variation map of primer compound L is came from the primers B09 and D19, and this distinctive primer compound L is further marked as L3-18. According to following table 6, the nucleotide sequence of L3-18 includes the sequence length of 2477 bp.

TABLE 6

| The marked ID of primer compound | Sequence Length (bp) | Sequence |
| --- | --- | --- |
| L3-18 | 2477 | ctggggacttcatgcgggagatacaatgacaaccgatattccgactgt tttcactttagccggaaatatatcttttgatattaaagatgagtctgg tgaggtaattggatctgctgttgcttcgaaagatactagaaagatagt cattacttttcacagcacggagcagacctctcaaacacagggaaaat tgacggggccttctcaatttttttacattgggatgttgaacaggtttc tcgagttgtgggcgtaagaataattgcactgtcagtggtcaaaagttt acttgagaggagggtaaaaatgtgacgaggatgacagctaaagtggcg agaactgggcatttgttcgcggtcttattgattttgatgagtatgtta acaggcttagtgacaagtggcagttcagttgtgacagccactgctaac attcgcccaacctataaaaccaatgctaatggtacctatccagaaaat tcgtggcaggtcacgggacaacaaaatgtgatcaatcaacgcggcggg gatcaagtttcagggtgggataacaatacaacatgggatggtgatgcg actaataccacgaattatacctgaaatttggtgacccaataatccgg attatcagattcgaaaatatgctaaagagacgaatacccccggattgt acgacgtttatttgaacgtcaaaggcaatacacagcaaaatgtgaagc ctgtagatattgtcttagttgttgatatgtctgggtcaatggagttca acagatataacacgaatcgagccggtgctgttcgtacaggtgttaaga atttcttgacatctattcaaaacgccggtctgggtaattacgtcaatg ttggtttaattgggttttctagtcctggttatatcggtggcgaatcgg gttatattagtgtcaaattaggcaaagcaggtaatgccagccagcaac aagcgattaatggtgcattgaatccaaggtttcaagggggtacgtata cgcagattggtttgcggcaaggatcagccatgctgaatgcggacacca gtggcaataaaaaaatgatgattttgttaactgatggacgtgccgact ttttctaacaaggtgataaattcagagtggataaatggcacattgtat ggcactaattttggatccagaagagatgaacccagcgataccgcacaa cttcgatggccgtacaccgatagttcaggtaataccatatatgatact tggcccgcaacattaggtgaggctaagaatgcaaaagatagcggtaat gaggtgcacgctttaggcattcaactggctgacgaccgccaatacatg acaaaagaaaaaatacgccaaaacatgcaacttattaccaattcaccg gatttatacgaagatgctgatagtgccgacgctgttgaggcttatttg aacaatcaggcaaaggatattatcaaaaattttaatactgtcaccgat ggcacgatcacagacccgattggtacgcaatttcaatatgcaaacaac caggcgaccgttacgagtgtcggcaagcaaactgtgccagcaagtgag ttgccaagtgcggcgatccaagatggtcaattgacggtgaatcacatg aacttgggtcaggatcaggaagttcaaatccattatcaagtacggatc aaaacagaggatgctggcttcaagcctgatttttggtaccaaatgaat ggtgaaacattgttgacaccaaaagcgggcgctgccgctgttgactttt gggattccttcaggcagggcaccagcaactacagtttatgtgcagaag caatggcgccagttaagcaatcaatcgttaccggatacgctcaacgtc acggtgcagcgaaaagtggctgacggttcgcttgatccaaattggcaa cagaccttagtcctttaaaaaagctgataactggaaagctagctttacg gcacctgcgtataacaatcagggtcaaagtttttcatatgtcgttaag agtgaagatgcctcgggaattgatttgagttcgtttatcagttctcaa aatatggatcagcaaacagcaacgttgactttgacaaatcagcagtat ggttttcaatttcagaaaaaaacaaccgatggtactgatttatcagca gatcagttgaaggccatgcagtttaacttaacccagtacagcgataac agttttcagcaggtatccaaaaccaacgccatcacgtcaacggatctg caggcactagcgccggggtattacggtattcaggaagctgcagcacct acaggttatcaacttgatgggacaatgtatcttttcagctaacgtct gatggcaatggcaataccatggcacaaaggacaatgtgacatcaggg agtgttattaatggccagcagactttgaatcctgttggtgataagtca gatgattttacggtgaccgggtagatct |

Figure 4:
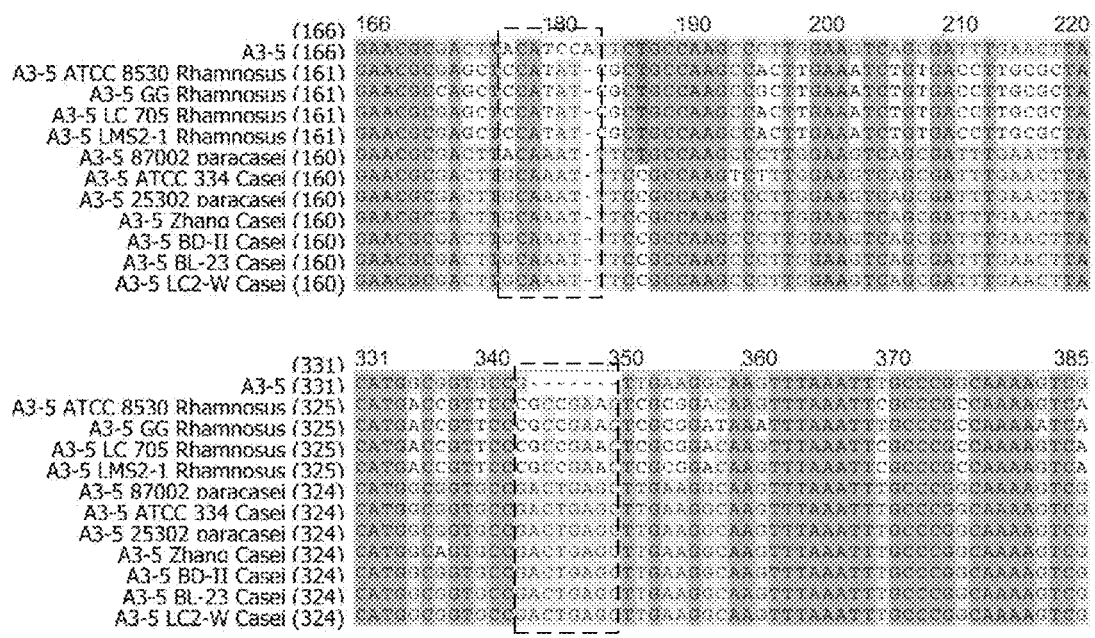
FIG. 4 is a comparing RAPD genetic variation map of A3-5.
Figure 5:
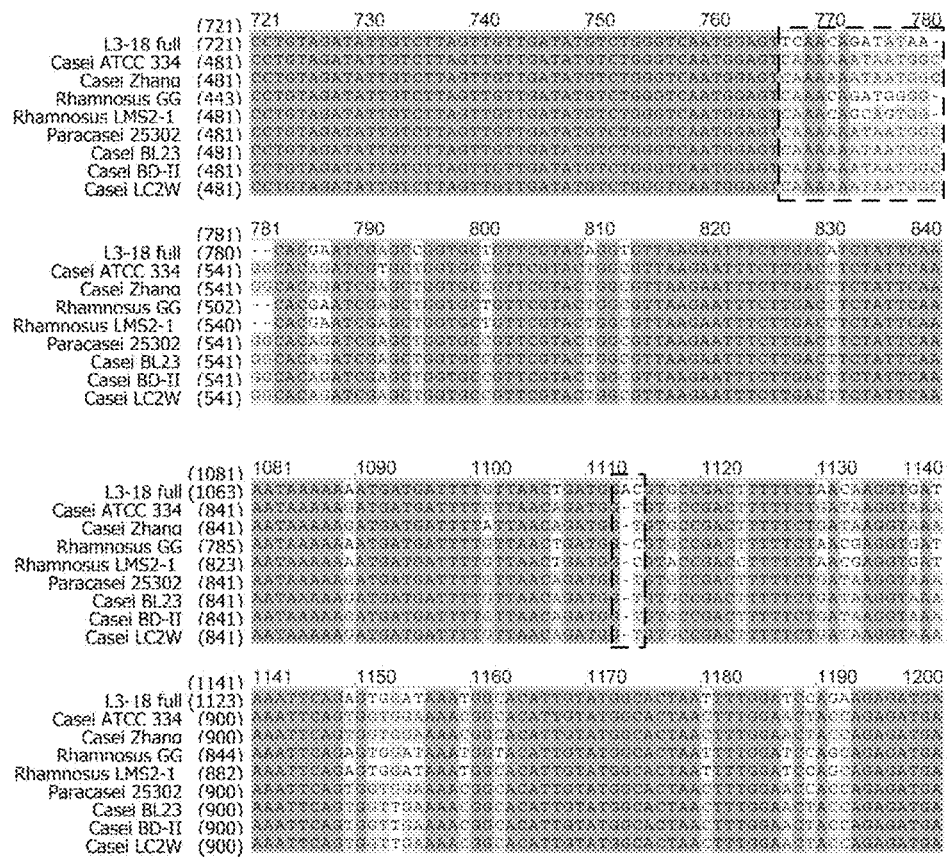
FIG. 5 is a comparing RAPD genetic variation map of L3-18.

Through above-presented experiment results of PCR and RAPD, it is able to initially know that the A3-5 and L3-18 may include the unique sequence fragments of the *Lactobacillus paracasei* subsp. *paracasei* NTU 101. Therefore, in order to further confirm whether the A3-5 and L3-18 does include the unique sequence fragments, the homologous DNA sequence data from Genbank are used to make a sequence comparison with the A3-5 and L3-18. Please refer to FIG. 4 and FIG. 5, there are shown comparing RAPD genetic variation maps of the A3-5 and L3-18. After comparing with the homologous DNA sequence, the rectangle dashed line encloses a unique sequence fragment of A3-5 in FIG. 4, and this unique sequence fragment in A3-5 can be used for carrying out the strain (mutant) identification of the NTU 101 by using the DNA molecular marker technology. Moreover, the rectangle dashed line also encloses a unique sequence fragment of L3-18 in FIG. 5, and this unique sequence fragment in L3-18 can also be used for carrying out the strain (mutant) identification of the NTU 101 by using the DNA molecular marker technology.

Because both the A3-5 and L3-18 include the unique sequence fragment for identifying the NTU 101, it needs to further check the specificity of the DNA molecular marker of the A3-5 and L3-18. As shown in following table 7, which records and lists a plurality of primers for checking the specificity of the DNA molecular marker of the A3-5 and L3-18.

TABLE 7

| Target | Primer ID | Sequence (5'→3') |
|--------|-----------|------------------|
| L3-18  | 18FF      | ATGCGGGAGATACAATGACAACCG |
|        | 18FR      | CCCGTCAATTTTCCCTGTGTTTGA |
|        | L3-18F    | GAAAATTGACGGGGCCTTCTCA |
|        | L3-18R    | ACTGACAGTGCAATTATTCTTACGCCC |
|        | L3-18F2   | AAAACCAATGCTAATGGTACCTATCCAG |
|        | L3-18R2   | GGGGTCACCAAATTTCAGGTAAGAAT |
|        | L3-18F3   | GTCTGGGTCAATGGAGTTCAACAGATATA |
| A3-5   | A3-5F     | GGCATGGCGGTGCCGTTGAA |
|        | A3-5R     | ATCCCCGAATGGTGCCAGCA |
|        | A3-5F2    | GCCGAACGCGACTTACATCCA |
|        | A3-5R2    | GGCAATTTAAACTTGCCTTCAACGG |
|        | A3-5F3    | CGCCGAACGCGACTTACATC |
|        | A3-5R3    | GGCAAATTTAAACTTGCCTTCAACG |
|        | A3-5F4    | GCGACTTACATCCATTCTGCCAAG |
|        | A3-5R4    | GAAATTTAAACTTGCCTTCAACGGCA |
|        | A3-5F5    | GCCGAACGCGACTTAGATCCATT |
|        | A3-5R6    | TAAACTTGCCTTCAACGGCACCG |
|        | A3-5F6    | GCCGAACGCGACTTACAGCCA |
|        | A3-5R7    | TTTAAACTTGCCTTCAACGGCAC |

Figure 6A:
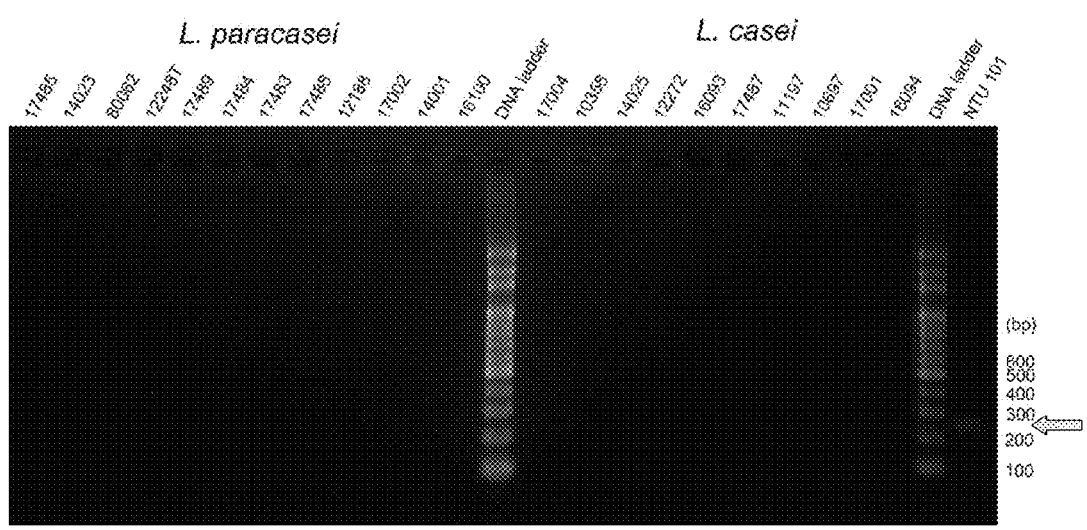
FIG. 6A and FIG. 6B are specificity test diagrams of the RAPD genetic variation map of A3-5.
Figure 6B:
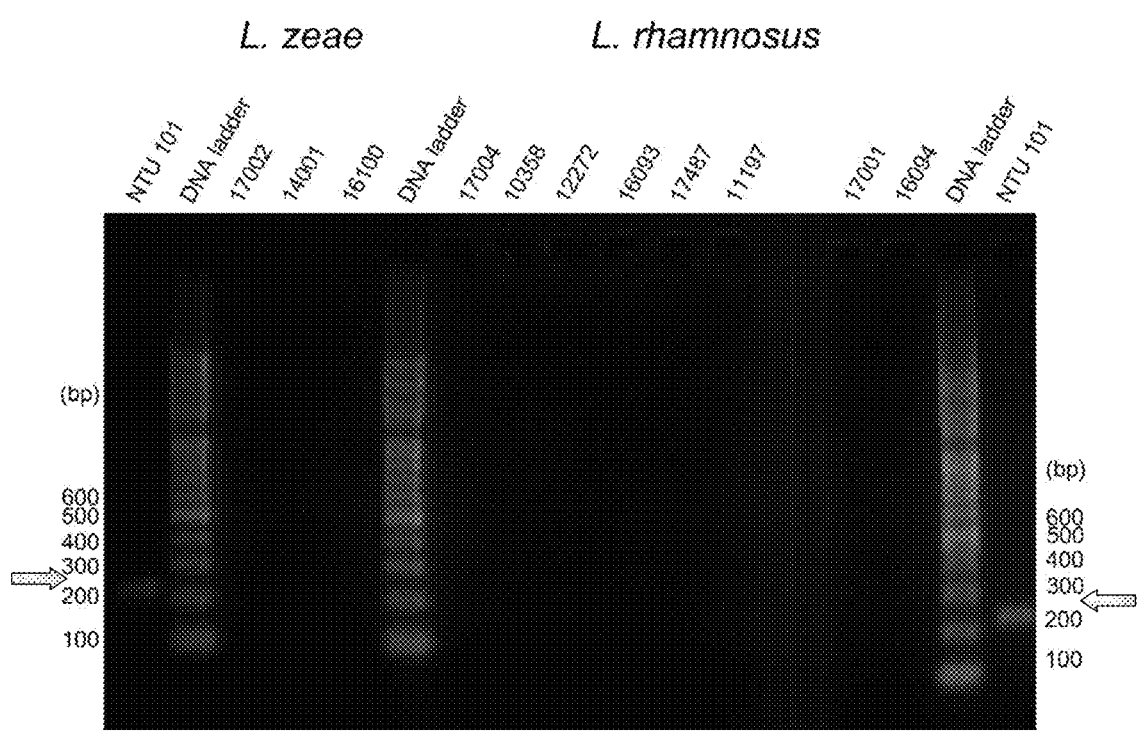

Please refer to FIG. 6A and FIG. 6B, there are shown specificity test diagram of the RAPD genetic variation map of A3-5. As shown in FIG. 6A and FIG. 6B, after completing the specificity test by using the primers listed in table 7, it is able to find that the A3-5 (F3/R3) indeed includes the specificity of NTU 101, so that the nucleotide sequence of the A3-5 can be used for carrying out the strain (mutant) specificity of the *Lactobacillus paracasei* subsp. *paracasei* NTU 101 proposed by the present invention. Moreover, as shown in Sequence Listing, the primer compound A3-5F3 is identified as SEQ ID NO 4 and includes the sequence length of 20 bp; besides, the primer compound A3-5R3 is identified as SEQ ID NO 5 and includes the sequence length of 25 bp.

Thus, through the descriptions, the *lactobacillus* mutant of *Lactobacillus paracasei* subsp. *paracasei* NTU 101, the nucleotide sequence for NUT 101, and the primers for nucleotide sequence of NTU 101 of the present invention has been completely introduced and disclosed; in summary, the present invention has the following advantages:

In the present invention, the nucleotide sequence for *Lactobacillus* NTU 101 and the primers for the nucleotide sequence are proposed in order to facilitate the person skilled in *Lactobacillus* filed capable of carrying out the strain (mutant) identification of the *Lactobacillus* NTU 101 according to the present invention. Moreover, the person skilled in *Lactobacillus* filed can also rapidly complete the strain (mutant) identification of the *Lactobacillus* NTU 101 by using DNA molecular marker technology, without culturing any isolated *Lactobacillus* strain or live *Lactobacillus* bacteria.

The above description is made on embodiments of the present invention. However, the embodiments are not intended to limit scope of the present invention, and all equivalent implementations or alterations within the spirit of the present invention still fall within the scope of the present invention.

---

What is claimed is:

1. A *Lactobacillus* mutant, which is a *Lactobacillus paracasei* subsp. *paracasei* NTU 101 having a nucleotide sequence of SEQ ID NO 1, and deposited with with Deutsche Sammlung von Mikroorganismen und Zellkulturen GmbH (DSMZ) on Nov. 18, 2013, wherein the accession number of the *Lactobacillus paracasei* subsp. *paracasei* NTU 101 is DSM 28047; wherein the nucleotide sequence of *Lactobacillus paracasei* subsp. *paracasei* NTU 101 can be identified by using following primers:
   (1): A3-5F3 CGCCGAACGCGACTTACATC (SEQ ID NO 4); and
   (2): A3-5R3 GGCAAATTTAAACTTGCCTTCAACG (SEQ ID NO 5).

2. The *Lactobacillus* mutant of claim 1, wherein when the *Lactobacillus paracasei* subsp. *paracasei* NTU 101 would produce lactic acid after being cultured in a culture medium containing at least one specific carbon source for at least 24 hours.

3. The *Lactobacillus* mutant of claim 2, wherein the specific carbon source is selected from the group consisting of: Glucose, Galactose, D-ribose, Xylose, Fructose, α-Lactose, Maltose, Sucrose, Trehalose, Raffinose, myo-Inositol, Sorbitol, D-mannitol, Citric acid, Dextrin, Starch, and Molasses.

4. The *Lactobacillus* mutant of claim 1, wherein when the *Lactobacillus paracasei* subsp. *paracasei* would produce lactic acid after being cultured in a culture medium containing at least one specific nitrogen source for at least 24 hours.

5. The *Lactobacillus* mutant of claim 4, wherein the specific nitrogen source is selected from the group consisting of: Yeast extract, Beef extract, Peptone, Soytone, Tryptose, Corn-steep liquor, Casein, Urea, Ammonium citrate, and Ammonium sulfate.

\* \* \* \* \*

SEQUENCE LISTING

<160> NUMBER OF SEQ ID NOS: 5

<210> SEQ ID NO 1
<211> LENGTH: 838
<212> TYPE: DNA
<213> ORGANISM: Lactobacillus mutant
<220> FEATURE:

<400> SEQUENCE: 1

```
agatctagcg ccattggtct tgaaagctcg cctgttgctg cagcattggc        50
aggattgcgc gcaaatgaag cgcgttacat ctggaataag tataaggaac       100
cttatatcac ttatccggct gccgaaaaac ctgacagtct cgcatgggtt       150
aatgaaattc tcgccgaacg cgacttacat ccattctgcc aagcccttgg       200
aagtcagcga tttgaactta ccggatttgc actgggttga ggtttactat       250
caagacggat tagccatcaa cgtgatgtat agcttgtccg accccaaaaa       300
acgcgcggtt ggctttaaac ttagcgatgg catggcggtg ccgttgaagg       350
caagtttaaa tttgcccggc aaaagtcgaa gcttgctggc accattcggg       400
gatctttttt cgtcatcaag gtcagccatt gaaaaaagac aactttttaa       450
cttgataagc ttacacatac aaaaaacggc cacggtgatg ttcctcaata       500
ttggaggtat gacatcaccg tggccatttt tgcgtataat cgtttaaaca       550
aagactgaaa tggccagctg aatatttaga acggtgatca cacccgtcag       600
```

```
aaaatagccg acccaccgca cgagttgcga attaacgtgg atacccatca            650
aatcacgccg attcgtcaag gccaccaacg ggaaaagcgt aaatggcaag            700
gcaatgctca atgacacctg cgcatagaca ataacttgct caaagttgtg            750
ttcgctaaaa ccgatcatga agccaatcac catgatggga atgagcgtca            800
caagtcgcgt cagcaacctc cgctcccaca atggcgct                         838

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 2
gtttctctcc                                                         10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 3
agcgccattg                                                         10

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 4
cgccgaacgc gacttacatc                                              20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotides.

<400> SEQUENCE: 5
ggcaaattta aacttgcctt caacg                                        25
```